United States Patent [19]
Lurie et al.

[11] Patent Number: 5,827,893
[45] Date of Patent: Oct. 27, 1998

[54] MECHANICAL AND PHARMACOLOGICAL THERAPIES TO TREAT CARDIAC ARREST

[76] Inventors: Keith G. Lurie, 4751 Girard Ave. S., Minneapolis, Minn. 55409; Karl Lindner, Steinhovelstr 9, Ulm 89075, Germany

[21] Appl. No.: 625,733

[22] Filed: Mar. 29, 1996

[51] Int. Cl.⁶ .................................................. A61K 25/00
[52] U.S. Cl. ...................... 514/653; 530/315; 530/309.2; 530/309.3
[58] Field of Search .................................. 514/360, 653; 530/315, 389.2, 389.3

[56] References Cited

U.S. PATENT DOCUMENTS 4,693,243   9/1987   Buras ................................ 128/207.15

FOREIGN PATENT DOCUMENTS

94/11045   of 0000   WIPO.

OTHER PUBLICATIONS

Todd J. Cohen et al., "Active Compression–Decompression," *JAMA*, 267, 2916, (1992).

Mickey S. Eisenberg et al., "Long–Term Survival After Out–of–Hospital Cardiac Arrest," *NEJM*, 306, 1340, (1982).

T.A. Fischer et al., "Curent Status Phosphodiesterase Inhibitors in the Treatment of Congestive Heart Failure," *Drugs*, 44, 928, (1992).

Karl H. Lindner et al., "Effect of Vasopressin on Hemodynamic Variables, Organ Blood Flow, and Acid–Base Status in a Pig Model of Cardiopulminary Resuscitation," *Anesthesia & Analgesia*, 77, 427, (1993).

Karl H. Lindner et al., "Release of Endogenous Vasopressors During and After Cardiopulmonary Resuscitation," *Br. Heart J.*, 75, 145, (1996).

Karl H. Lindner et al., "Effects of Active Compression–Decompression Resuscitation on Myocardial and Cerebral Blood Flow in Pigs," *Circulation*, 88, 1254, (1993).

Karl H. Lindner et al., "Vasopressin Improves Vital Organ Blood Flow During Closed–Chest Cardiopulmonary Resuscitation in Pigs," *Circulation*, 91, 215, (1994).

Keith G. Lurie, "Active Compression–Decompression CPR: A Progress Report," *Resuscitation*, 28, 115, (1994).

James T. Niemann, "Cardiopulmonary Resuscitation," *NEJM*, 327, 1075, (1992).

Jeffrey B. Sack et al., "Survival from In–Hospital Cardiac Arrest with Interposed Abdominal Counterpulsation During Cardiopulmonary Resuscitation," *JAMA*, 267, 379, (1992).

Ian G. Stiell et al., "High–Dose Epinephrine in Adult Cardiac Arrest," *NEJM*, 327, 1045, (1992).

S.P. Woodhouse et al., "High Dose and Standard Dose Adrenaline Do Not Alter Survival, Compared with Placebo, in Cardiac Arrest," *Resuscitation*, 30, 243, (1995).

*Primary Examiner*—Keith D. MacMillan
*Attorney, Agent, or Firm*—Schwegman, Lundberg, Woessner & Kluth, P.A.

[57] ABSTRACT

A pharmaceutical composition is provided which comprises vasopressin and an adrenergic agent in combination with a pharmaceutically acceptable carrier. The pharmaceutical composition is effective to increase arterial blood pressure so as to enhance arterial blood flow to the brain and heart when administered to a patient suffering from cardiac arrest. A method of treating a patient in cardiac arrest is also provided, which method comprises the administration of the pharmaceutical composition during the administration of CPR.

28 Claims, 3 Drawing Sheets

MECHANICAL AND PHARMACOLOGICAL THERAPIES TO TREAT CARDIAC ARREST

BACKGROUND OF THE INVENTION

In the United States each year, more than 350,000 people die from cardiac arrest prior to arriving in the hospital. Even when patients are resuscitated initially, more than half die in the hospital within the first 24 hours. Eisenberg et al., *NEJM*, 306, 1340 (1982). Despite more than three decades of the practice of manual external chest compression or standard CPR, together with epinephrine administration, less than 5% of patients who suffer a cardiac arrest survive. Niemam, *NEJM*, 327, 1075 (1992). Though time to initiation of standard CPR is a critical factor in determining outcome, the inherent limitations of manual external chest compression are perhaps an even greater reason for the poor survival statistics. In light of the tremendous amount of time, money and energy involved in basic CPR performance and training, these statistics become even more disheartening. Although pharmacologic therapy, specifically intravenous epinephrine and antiarrhythmic therapies, have served to improve outcomes in some patients, the role of vasopressor agents during CPR remains controversial. Stiell et al., *NEJM*, 327, 1045 (1992).

Over the past 35 years since standard manual external chest compression was described, there have been a number of advances in the mechanical means available to improve overall CPR efficacy. Based on the assumption that increases in intrathoracic pressures will increase cardiac output during ventricular fibrillation, techniques such as the circumferential vest and active compression and decompression (ACD CPR) have been developed. Lurie, *Resuscitation*, 28, 115 (1994). In an effort to enhance filling of the coronary arteries and enhance venous return during the diastolic or decompression phase of CPR, techniques such as interposed abdominal counterpulsion CPR and use of a rapidly inflating and deflating intra-aortic balloon pump, as well as ACD CPR have been used. Sack et al., *JAMA*, 267, 379 (1992).

In addition to the research conducted on mechanical means to improve the efficacy of CPR, there has been a renewed interest in developing pharmacological therapies to improve the vital organ blood flow and overall survival of patients who have suffered a cardiac arrest. Such therapies typically include the intravenous administration of epinephrine during the performance of CPR. Epinephrine is an arterial constrictor, and its use is intended to enhance patient blood pressure during the resuscitation process. Even with epinephrine, however, survival after cardiac arrest is poor. Furthermore, recent studies have demonstrated no added benefit from doses of epinephrine higher than the traditional dose. Stiell et al., cited supra. Recent studies show no benefit of high or low dose epinephrine with placebo. (Woodhouse et al., *Resuscitation*, 30, 243 (1995).

Applicant has described the concurrent administration of a venodilator (nitroglycerin) and an arterial constrictor (epinephrine) during CPR in published PCT application WO 94/11045, which discloses a method for resuscitating a patient from cardiac arrest, comprising actively inducing venous blood transport into the heart and arterial blood transport from the heart; ventilating the patient's lungs; administering to the patient concurrently with said inducing and ventilating steps an arterial constrictor sufficient to increase the patient's arterial blood pressure; and administering to the patient concurrently with said inducing and ventilating steps an amount of a venodilator sufficient to enhance arterial blood flow to the patient's brain and heart.

However, a continuing need exists for improved methods and pharmaceutical compositions for use during CPR, which result in enhanced long term survival among at least certain populations of cardiac arrest patients. Such methods and compositions would preferably enhance blood circulation and delivery of oxygenated blood to patient tissue, particularly heart and/or brain tissue, without significantly lessening patient blood pressure.

SUMMARY OF THE INVENTION

The present invention provides a pharmaceutical composition and method for resuscitating patients suffering from cardiac arrest, particularly patients experiencing ventricular fibrillation, asystole, electromechanical dissociation (EMD), and the like. Surprisingly, it has been found that the use of vasopressin when combined with an adrenergic agent such as epinephrine or aminophylline, leads to enhanced vital organ blood flow during CPR when compared with standard epinephrine therapy. Thus, the present invention provides a pharmaceutical composition comprising vasopressin and an adrenergic agent in combination with a pharmaceutically acceptable carrier. Preferably, the adrenergic agent is selected from adrenergic agonists such as epinephrine, dopamine, norepinephrine, isoproterenol, phenylephrine, dobutamine or methoxamine. Most preferably, the adrenergic agonist is epinephrine. The adrenergic agent can also be an indirect sympathomimetic agent which prevents the degradation of cAMP, i.e., a phosphodiesterase (PDE) inhibitor. A representative PDE inhibitor is aminophylline. A combination of more than one adrenergic agent, for example epinephrine and isoproterenol, plus vasopressin will also enhance vital organ blood flow during CPR. In this manner, adrenergic agents with relatively great $\alpha$ and/or $\beta$ adrenoceptor selectivity can be combined and added to vasopressin therapy.

It is preferred that the vasopressin and the adrenergic agent are administered to a patient suffering from cardiac arrest and undergoing active inducement of venous blood transport into the heart and arterial blood transport from the heart, in amounts effective to increase arterial blood pressure so as to enhance arterial blood flow to the brain and heart. More preferably, the vasopressin will be present in the composition at a dose range of about 10 units to 120 units and the epinephrine is present at a dose range of about 0.25 mg to 3.0 mg.

Applicant has made the surprising discovery that the administration of a vasodilator, such as nitroglycerin, to a patient in cardiac arrest concurrent with vasopressin or an adrenergic agent attenuates some of the vasoconstrictor effects of the latter agents on the coronary arterial bed. The administration of a vasodilator serves to dilate the coronaries and decrease preload without a significant effect on afterload when administered concurrently with the pharmaceutical composition of the present invention. Thus, the pharmaceutical composition may optionally include an amount of a vasodilator effective to increase myocardial blood flow. Preferably, the vasodilator will be nitroglycerin and will be present in the composition at a dose range of about 10 $\mu$g to 200 $\mu$g.

In addition to the vasopressin and the adrenergic agent, the pharmaceutical composition of the present invention can also include other active substances which are intended to enhance the therapeutic effectiveness of the composition. For example, the pharmaceutical composition can also include mannitol in an amount effective to reduce swelling of the brain, heart, and/or kidneys, due to mannitol's osmotic properties. Additionally, mannitol can also enhance patient blood pressure. Mannitol can be provided at a total dosage in the range from about 1 g to 100 g, preferably from about 5 g to 50 g.

The pharmaceutical compositions of the present invention may optionally also include a calcium channel blocker, such as diltiazem, verapamil, nifedipine, and the like, in an amount effective to inhibit calcium overload. Typically, diltiazem would be present in a dosage from about 0.5 mg to 60 mg, preferably from about 0.5 mg to 20 mg. Verapamil would be present in a dosage from about 0.5 mg to 60 mg, preferably from about 0.5 mg to 5 mg. Nifedipine would be present in a dosage from about 0.2 mg to 10 mg, preferably from about 0.5 mg to 5 mg.

The present invention also provides a method useful for treating patients suffering from cardiac arrest with the present composition. Specifically, the method of the present invention comprises active inducement of blood transport and lung ventilation concurrently with the administration of vasopressin and an adrenergic agent to both increase arterial blood pressure and to enhance arterial blood circulation. Preferably, the adrenergic agent used in the practice of the present method is selected from the group consisting of epinephrine, dopamine, isoproterenol, norepinephrine, phenylephrine, dobutamine, methoxamine and a phosphodiesterase inhibitor. Most preferably, the adrenergic agent is epinephrine or aminophylline.

Use of aminophylline can be particularly useful in patients with asystole as this drug enhances endogenous sympathetic responsivity and can also block the bradycardic effects of adenosine.

DETAILED DESCRIPTION OF THE INVENTION

Figure 1A:
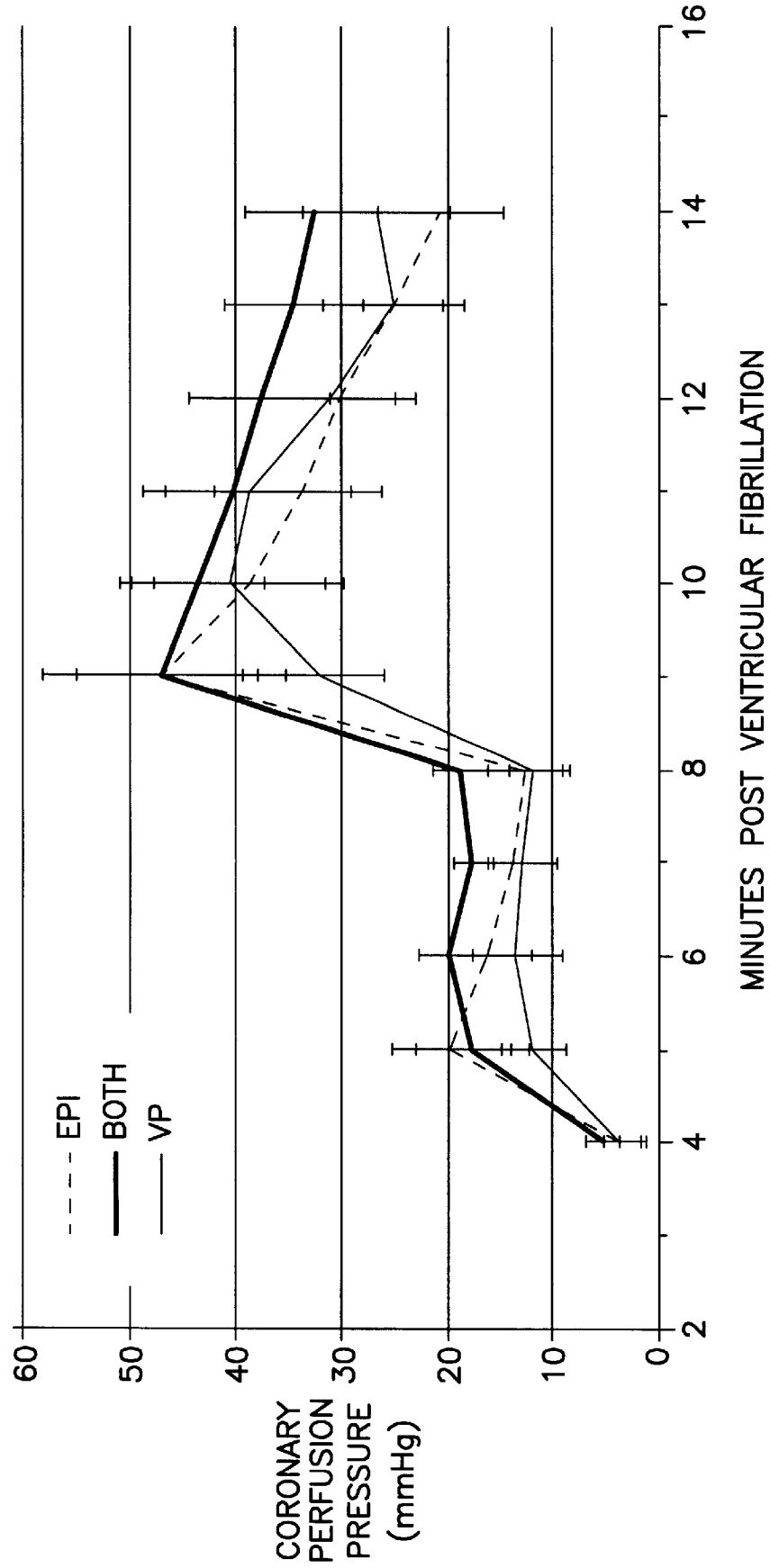
FIG. 1a is a graphical depiction of the coronary perfusion pressures (CPP) (diastolic aortic minus right arterial pressures) of pigs (n=6 per group) resuscitated from ventricular fibrillation with epinephrine alone (EPI) 40 $\mu$g/kg, vasopressin alone (VP) 40 units, or a combination of epinephrine and vasopressin (EPI+VP) which illustrates that the combination of vasopressin+epinephrine leads to more rapid, higher, and more sustained coronary perfusion pressures (mean±SEM) than either agent alone. After 14 minutes of CPR and 10 minutes after drug, the mean coronary perfusion pressure was 50% greater with vasopressin plus epinephrine then epinephrine alone. The benefit of the combined approach is similarly seen after 1 minute where the higher perfusion pressure are seen on the combined regimen versus vasopressin along.

The present invention provides a pharmaceutical composition and method useful for treating patients suffering from cardiac arrest. Cardiac arrest generally refers to conditions resulting in the loss of effective heart function and the loss of effective blood circulation. Specific conditions treatable by the present invention include ventricular fibrillation, characterized by rapid contractions and twitching of the heart muscle; asystole, characterized by the substantial absence of contractions of the heart; and electromechanical dissociation (EMD), characterized by the persistence of electrical activity in the heart without associated mechanical contractions.

A. Methods of Cardiopulmonary Resuscitation

The method of the present invention comprises active inducement of blood transport and lung ventilation concurrently with the administration of certain drugs selected to both increase arterial blood pressure and to enhance arterial blood circulation. The active inducement of blood transport includes both the transport of venous blood from the extremities and abdomen, into the thorax and heart, as well as the transport of blood from the heart into the lungs and arterial system. Both the induced blood transport and the lung ventilation are preferably achieved by certain advanced CPR methods, such as ACD CPR, as described in Cohen et al., *JAMA*, 267, 2916 (1992), and interposed abdominal compression (IAC), as described in Neimen, *N. Engl. J. Med.*, 327, 1075 (1992). Induced blood transport and lung ventilation can be achieved, but to a lesser extent, with standard chest massage and CPR techniques. Optionally, additional measures will be taken to provide lung ventilation, such as use of an endotracheal tube, mouth-to-mouth resuscitation, or the like.

B. Pharmacologic Therapy for Patients in Cardiac Arrest

While these enhanced methods for CPR can by themselves improve the chances for patient survival when compared to conventional CPR, the present invention is based on the discovery that the vital organ blood flow (with conventional CPR and in particular with the enhanced CPR techniques described above) can be further improved by administering the combination of vasopressin and an adrenergic agent. It has also been discovered that the administration of vasodilators, such as nitroglycerin, in combination with the pharmaceutical composition of the present invention, can attenuate some of the intense vasoconstrictor effects of the exogenous vasopressors on the coronary arterial bed and thereby further improve myocardial blood flow.

1. Vasopressin

Vasopressin is usually called antidiuretic hormone (ADH) by physiologists and biochemists, because it decreases urine flow by increasing the resorption of water from the distal convoluted tubules and collecting ducts of the kidney. Not only does it promote water retention but under certain circumstances, it increases the excretion of sodium and chloride. The effect is a decrease in the osmolarity of the extracellular fluid. In addition to its antidiuretic effects, vasopressin also stimulates vascular smooth muscles.

When compared with "optimal" doses of epinephrine administered during CPR, vasopressin administration results in higher levels of myocardial perfusion, greater cerebral perfusion, and greater chances for resuscitation. Lindner et al., *Anesthesia & Analgesia*, 77, 427 (1993). Furthermore, the higher the level of vasopressin in humans in cardiac arrest, the greater the chances of survival. Lindner et al., *Br. Heart J.*, 75, 145 (1996). In contrast, the higher the level of endogenous levels of catecholamines in patients in cardiac arrest, the worse the chances of survival. Vasopressin is effective as an arterial constrictor under conditions of severe acidosis and the duration of action of vasopressin appears to be 3–4 times longer than comparable doses of epinephrine.

Lindner et al., *Circulation*, 91, 215 (1994). Vasopressin is commercially available from Park Davis, Morris Plains, N.J.

2. Adrenergic agents a. Adrenergic agonists (direct-acting sympathomimetics)

Adrenergic agonists increase the heart rate, enhance atrioventricular conduction, and increase the strength of the heart beat (positive inotropic action). They also induce lipolysis and thus increase the concentration of plasma free fatty acids. These effects are achieved, in part, through the activation of the adenylylcyclase system and the intermediation of 3',5'-cyclic adenosine monophosphate (cyclic AMP). Adrenergic agonists suitable for use in the present invention include, but are not limited to, epinephrine, norepinephrine, dopamine, dobutamine, isoproterenol, phenylephrine, methoxamine, and the like. Preferably, the adrenergic agonist employed is epinephrine.

i. Epinephrine

Epinephrine is the predominant sympathomimetic in the adrenal medulla and stimulates both $\alpha$ and $\beta$ adrenoceptors. $\beta_1$ as well as $\beta_2$ stimulation may be particularly important in the heart especially immediately after direct current shock. It is liberated in conditions of stress and vigorous exertion. At low doses or low intravenous infusion rates, it is possible to stimulate the heart and relax bronchioles and at the same time decrease the diastolic blood pressure. However, the vasoconstrictor effect is stronger than the vasodilator effect, so that at higher doses there is a net increase in vascular resistance and extreme hypertensive crisis can occur with overdoses. Epinephrine is the drug of choice in the management of allergic emergencies, such as anaphylaxis, edema, and the like. Epinephrine is also a resuscitant for patients in cardiac arrest, however, the concomitant vasoconstriction is thought to place an unwanted load on a compromised heart. Epinephrine is commercially available from a number of companies.

b. Indirect Sympathomimetic Agents (Phosphodiesterase Inhibitors

The phosphodiesterase inhibitors have been recognized as potent inotropic and vasodilating drugs. In acute congestive heart failure, they increase cardiac output, decrease left pulmonary capillary wedge pressure, and reduce total peripheral resistance with an improvement in loading conditions of the failing heart. Their potency in reversal of symptoms of acute congestive heart failure is quite similar to, or even better than, treatment with intravenous catecholamines and sodium nitroprusside. A preferred PDE inhibitor for use in the present method is aminophylline. See Merck Index (11th ed.) at entry 477. Other suitable PDE inhibitors are disclosed by T. A. Fischer et al., *Drugs*, 44, 928 (1992).

3. Nitroglycerin

Nitroglycerin is a coronary dilator and a general relaxant of smooth muscle. Its actions are directly on the smooth muscle. It preferentially dilates capacitance veins when compared with system resistance arteries. In the doses used for prophylaxis or relief of acute attacks of angina pectoris, it dilates the capacitance veins, which decreases venous return, and the coronary arteries, which decreases arterial impedance.

C. Modes of Administration

Vasopressin and the adrenergic agent are preferably administered to the patient concurrently with or as soon as possible after the initiation of the enhanced CPR procedure, preferably being administered within from 0 to 60 minutes after such initiation, more preferably being administered from 0 to 10 minutes after such initiation. Both the initiation of CPR and the administration of the combination of vasopressin and an adrenergic agent should be initiated as shortly as possible after the cardiac arrest, with drug administration preferably beginning within 10 minutes of arrest. Administration of the combination dose of vasopressin and the adrenergic agent will preferably be repeated during procedures which last for more than 10 minutes, usually being repeated every 3 to 10 minutes.

The vasopressin and adrenergic agent can be administered by any technique which assures rapid absorption into patient circulation, preferably being administered parenterally, i.e., by injection or infusion, as intravenously, endotracheally, intracardiac, or by other parenteral routes. Intravenous injections will usually be made to a peripheral vein in a conventional manner. Endotracheal administration may also be performed and is particularly suitable if an endotracheal tube has been introduced in order to enhance lung ventilation and intravenous access is not immediately available. Devices and methods suitable for endotracheal administration of drugs according to the present invention are described in U.S. Pat. No. 4,693,243, the full disclosure of which is incorporated herein by reference. In the case of endotracheal administration, the total dosages described above for both the arterial constrictor and the venodilator will generally be increased in order to offset the inefficiencies of such an administration route. The dosages will usually be increased from two-fold to three-fold.

The vasopressin and the adrenergic agent will preferably be administered together in a single dosage or bolus, but could less preferably be administered separately and/or sequentially to the patient. It would also be possible to administer the total desired dosage of each of the vasopressin and the adrenergic agent in two or more discrete boluses, although such multiple administrations will generally be less preferred.

1. Dosage Forms

The pharmaceutical compositions of the present invention can be formulated for administration to a human patient in cardiac arrest in one or more unit dosage forms comprising an effective amount of vasopressin and an adrenergic agent, optionally further comprising mannitol and a calcium channel blocker, in combination with a pharmaceutically acceptable liquid carrier, such as distilled water, physiological salt solutions such as normal saline, buffers, and the like. Such pharmaceutical compositions will typically include a pharmaceutically acceptable preservative, and may include other components commonly employed in solutions suitable for intravenous and/or endotracheal administration such as nontoxic surfactants.

The present compositions are conveniently presented in pharmaceutical unit dosage forms, which will deliver single or multiple dosages of the active compounds parenterally, as by injection or infusion. Such dosage forms include prefilled bottles, ampules, plastic bags or preloaded syringes. Methods for preparing such pharmaceutical compositions and unit dosage forms are well known in the art and described in more detail in various sources including, for example, *Remington's Pharmaceutical Science,* 15th Edition, Mack Publishing, Easton, Pa.(1980), which is incorporated herein by reference.

The pharmaceutical dosage form suitable for injection or infusion can include sterile concentrated aqueous or aqueous-alcoholic solutions or dispersions which are adapted for extemporaneous dilution to yield sterile injectable or infusible solutions or dispersions. In all cases, the ultimate dosage form must be sterile, fluid and stable under the conditions of manufacture and storage. The liquid carrier or vehicle can be a solvent or liquid dispersion medium comprising, for example, a major portion of water in combination with ethanol, a polyol (for example, glycerol, propylene glycol, and liquid polyethylene glycols, and the like), vegetable oils, nontoxic glycerol esters, lipids (for example, dimyristoyl phosphatidyl choline) and suitable mixtures thereof. The proper fluidity can be maintained, for example, by the formation of liposomes, by the maintenance of the required particle size in the case of dispersion or by the use of nontoxic surfactants. Sterile injectable or infusible solutions are prepared by incorporating the vasopressin and an adrenergic agonist in the required amount in the appropriate solvent with various of the other ingredients enumerated above, and as required, followed by filter sterilization.

2. Dosages

The dosage of the vasopressin and an adrenergic agent in said composition can be varied widely, in accord with the size, age and condition of the patient. However, it is preferred that the vasopressin be administered in a dosage of from about 10 units to 120 units and that the epinephrine is administered in a dosage of from about 0.25 mg to 2.0 mg (i.e., total amount given to the patient at one time point during the procedure; administration may be repeated at successive time points as described below). Most preferably, the vasopressin is administered in a dosage of from about 10 units to about 50 units and the epinephrine is administered in a dosage of from about 0.75 mg to about 1.25 mg. The above dosages are the preferred ranges for adults and would be reduced somewhat for administration to children and infants.

The invention will be further described by reference to the following detailed examples.

D. Materials and Methods

Preparation of pigs

Healthy female domestic farm pigs (28–33 kgs) were fasted overnight and anesthetized with pentobarbital (20 mg/kg IV bolus followed by 2.5 mg/kg/hr IV infusion) via an ear vein. Once anesthetized, pigs were placed in the dorsal recumbent position and intubated using standard endotracheal intubation technique. They were ventilated during the preparatory phase of the experiment and after return of spontaneous circulation at the end of the experiment with a mechanical respirator (model 607, Harvard Apparatus Co., Inc., Dover, Mass.). The tidal volume was set at 450 cc and delivered between 11 and 15 breaths per minute with supplemental oxygen at 2 liters/minute. Normal saline solution will be administered intravenously through the preparative and study periods using an infusion pump (Flo-Gard 6201, Baxter Healthcare, Deerfield, Ill.).

The preparatory phase, which includes cannulation of both femoral arteries and the right jugular vein, as well as calibration of all instruments, takes approximately 2 hours. Once venous access was obtained, animals received normal saline solution at approximately 300–400 ml/hr to maintain diastolic right atrial pressures of 3–5 mm Hg. Arterial blood gases were analyzed every 30 minutes to insure adequate acid base status and oxygenation. Left ventricular and ascending aortic arch blood pressures were monitored using a single high fidelity micromanometer catheter (Millar, Houston, Tex.). This aorto-left ventricular catheter has a lumen for injecting radiolabeled microspheres and it was positioned, under fluoroscopic guidance, 15 minutes prior to initiation of VF. Right atrial pressures were monitored using a micromanometer catheter (Millar) inserted through a right jugular vein sheath. The micromanometer catheters were calibrated to atmospheric pressure immediately prior to inserting them into the pig.

A 5 French bipolar packing catheter (Daig, Inc., Minnetonka, Minn.), used to induce ventricular fibrillation (VF) with alternating current at 7 volts and 60 Hz, was inserted through a second right jugular vein sheath and positioned using fluoroscopy in the right ventricular apex. For withdrawal of reference blood samples to measure organ blood flow, a 7F catheter was advanced by femoral arterial access to the aortic arch. Body temperature was monitored continuously via a rectal probe (Yellow Springs Instrument Co., Yellow Springs, Ohio). Core temperatures were maintained between 36.5 and 38.5° C. using a heating pad. Five minutes prior to induction of VF, 5000 U of sodium heparin was be administered intravenously.

EXAMPLE 1

Applicants believe that concurrent administration of an adrenergic agonist together with vasopressin may help restore sinus nodal function and/or enhance myocardial contractility after cardioversion. Moreover, since vasopressin is more effective in acidosis and has a longer duration of action, Applicants believe that it may be better for helping to restore myocardial perfusion before cardioversion. This hypothesis was tested by comparing the effects of epinephrine (EPI) (40 ug/kg) versus vasopressin (VP) (0.3 units/kg) alone or in combination.

Figure 1B:
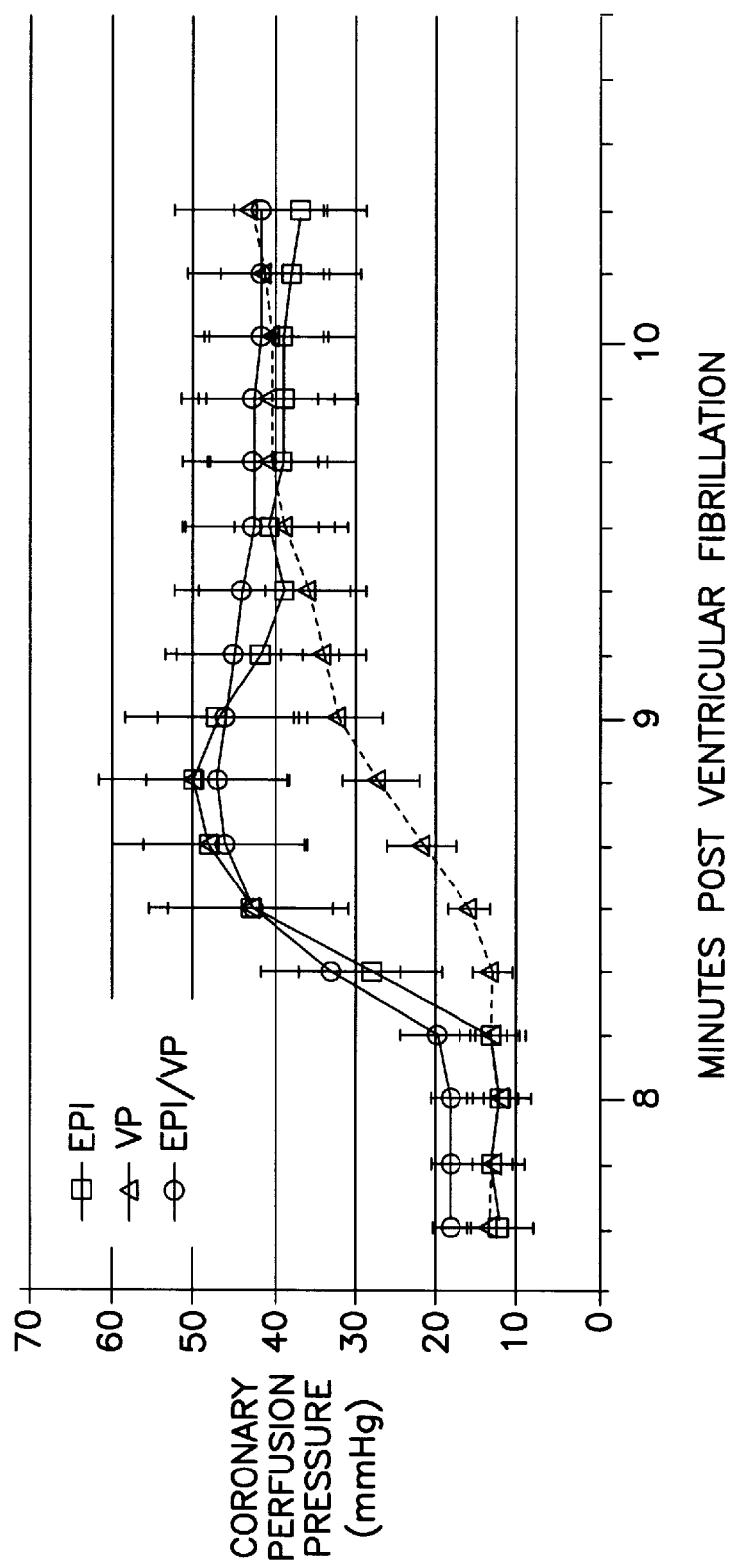
FIG. 1b shows the slower onset of effects of vasopressin compared with epinephrine alone or in combination with vasopressin.
Figure 2:
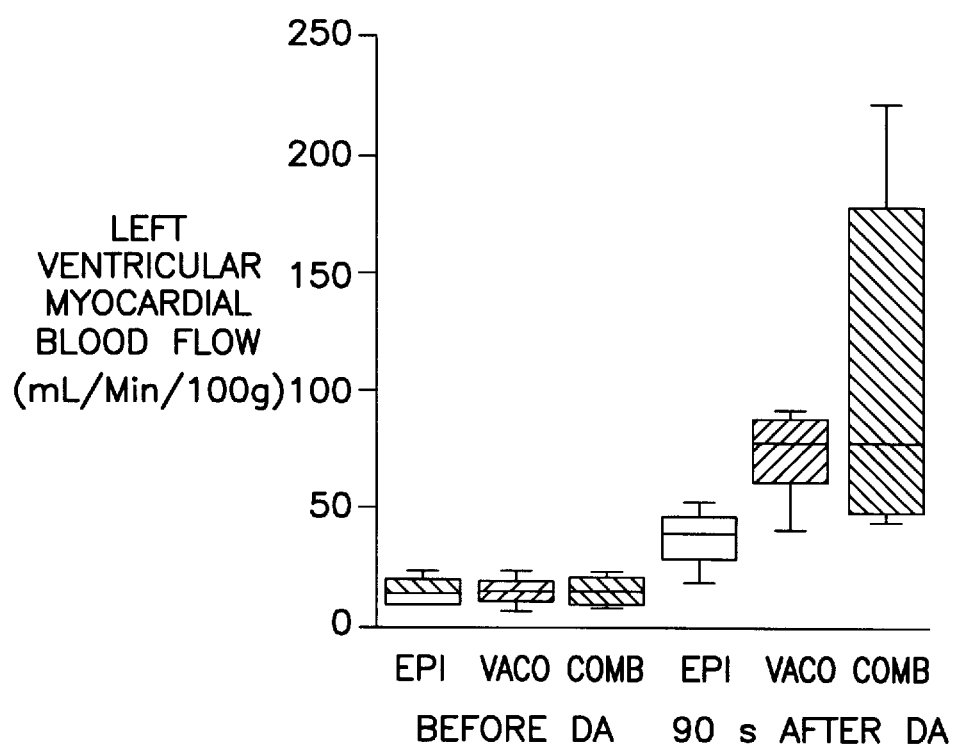
FIG. 2 is a graphical depiction of the results of a series of experiments conducted with higher concentrations of vasopressin (0.4 units/kg) and epinephrine (0.2 mg/kg) in a porcine model of ventricular fibrillation using standard CPR which illustrates that median (box=upper and lower quartiles, bars are maximal/minimal valves) myocardial and cerebral blood flows were increased by nearly 40% with the combination of these agents when compared with each drug alone.

With 6 pigs/group, using the protocol described hereinabove, the coronary perfusion pressures (CPP) (diastolic aortic minus right arterial pressures) can be seen in FIG. 1. The combination of vasopressin+epinephrine leads to more rapid and higher coronary perfusion pressures than either agent alone (FIG. 1). In a separate series of experiments with higher concentrations of vasopressin (0.4 units/kg) and epinephrine (0.2 mg/kg) in a porcine model of ventricular fibrillation using standard CPR, myocardial and cerebral blood flows were increased by nearly 40% with the combination of these agents when compared with each drug alone (FIG. 2).

EXAMPLE 2

COMBINATION VASOPRESSIN/NITROGLYCERIN THERAPY

Applicants have studied the effects of the combination of vasopressin therapy and nitroglycerin therapy in a porcine model of ventricular fibrillation using standard CPR. In this protocol, there were 7 pigs/group and an automated device was used to deliver standard CPR. Lindner et al., *Circulation* 88, 1254 (1993). Radiolabeled microspheres were used to measure myocardial blood flows during ventricular fibrillation prior to drug therapy and then 90 seconds after drug administration. After 3 minutes of ventricular fibrillation and 2 minutes of standard CPR, regional myocardial blood flow was 18.5 ml/min/100 g in the epicardium and 11 ml/min/100 g in the endocardium. After 10 minutes of ventricular fibrillation, and 7 minutes of standard CPR, vasopressin (0.4 units.kg)±nitroglycerin (5ug/kg) were administered and blood flow was again measured. Although no differences were seen in total myocardial blood flow, there was a significant increase in endocardial blood flow when nitroglycerin was used. It is the endocardial blood flow which is most comprised during CPR and which benefits from this combination of drugs.

All patents, patent documents and publications are incorporated by reference herein, as though individually incorporated by reference. While only certain preferred embodiments of this invention have been shown and described by way of illustration, many modifications will occur to those skilled in the art and it is, therefore, desired that it be understood that this is intended herein to cover all such modifications that fall within the spirit and scope of this invention.

What is claimed is:

1. A pharmaceutical composition comprising vasopressin and epinephrine in combination with a pharmaceutically acceptable carrier, wherein the vasopressin and the epinephrine are present in amounts effective to increase arterial blood pressure so as to enhance blood flow to the brain and heart when administered to patient suffering from cardiac arrest and undergoing cardiopulmonary resuscitation.

2. The pharmaceutical composition of claim 1, wherein the epinephrine is present at a dose range of about 0.25 mg to 3.0 mg.

3. The pharmaceutical composition of claim 1, wherein the vasopressin is present at a dose range of about 10 units to about 120 units.

4. The pharmaceutical composition of claim 1, further comprising mannitol, in an amount effective to inhibit edema when administered to the patient.

5. The pharmaceutical composition of claim 4, wherein the mannitol is present at about 5 g to 50 g.

6. The pharmaceutical composition of claim 1, further comprising a calcium channel blocker, present in an amount effective to inhibit calcium overload.

7. The pharmaceutical composition of claim 6, wherein the calcium channel blocker is diltiazem.

8. The pharmaceutical composition of claim 1 wherein the pharmaceutically acceptable carrier is a liquid.

9. The pharmaceutical composition of claim 8 wherein the pharmaceutically acceptable carrier is a physiological salt solution.

10. The pharmaceutical composition of claim 1, further comprising a vasodilator present in an amount effective to increase myocardial blood flow.

11. The pharmaceutical composition of claim 10 wherein the vasodilator is nitroglycerin.

12. The pharmaceutical composition of claim 11, wherein the nitroglycerin is present at about 10 µg to 200 µg.

13. A method for resuscitating a patient suffering from cardiac arrest, comprising: actively inducing venous blood transport into the heart and arterial blood transport from the heart; ventilating the patient's lungs; administering to the patient concurrently with said inducing and ventilating steps an amount of vasopressin effective to increase the patient's arterial blood pressure; and administering to the patient concurrently with said inducing and ventilating steps an amount of one or more adrenergic agonists effective to increase the patient's arterial blood pressure.

14. The method of claim 13, wherein active inducement of blood flow is achieved by active compression and active expansion of the patient's chest.

15. The method of claim 13, wherein active inducement of blood flow is achieved by alternatively compressing the patient's chest and the patient's abdomen or lower extremities.

16. The method of claim 13, wherein the vasopressin and the adrenergic agonist are administered essentially simultaneously.

17. The method of claim 13, wherein the adrenergic agonist is selected from the group consisting of epinephrine, dopamine, norepinephrine, isoproterenol, phenylephrine, dobutamine and methoxamine, or a combination thereof.

18. The method of claim 17, wherein the adrenergic agonist is epinephrine.

19. The method of claim 18, wherein about 0.25 mg to 3.0 mg epinephrine and about 10 units to 120 units vasopressin are administered in a single bolus.

20. The method of claim 19, wherein the bolus is administered intravenously.

21. The method of claim 19, wherein the bolus is administered endotracheally.

22. The method of claim 19, wherein the bolus further comprises about 5 g to 50 g of mannitol.

23. The method of claim 19, wherein the bolus further comprises a calcium channel blocker present in an amount effective to inhibit calcium overload.

24. The method of claim 19, wherein the bolus further comprises a vasodilator present in an amount effective to increase myocardial blood flow.

25. The method of claim 24, wherein the vasodilator is nitroglycerin.

26. The method of claim 25, wherein the nitroglycerin is present at about 10 µg to 200 µg.

27. A method for resuscitating a patient suffering from cardiac arrest, said method comprising: actively inducing venous blood transport into the heart and arterial blood transport form the heart; ventilating the patient's lungs; administering to the patient concurrently with said inducing and ventilating steps an amount of vasopressin effective to increase the patient's arterial blood pressure; and administering to the patient concurrently with said inducing and ventilating steps an amount of one or more phosphodiesterase inhibitors effective to increase the patient's arterial blood pressure.

28. The method of claim 27 wherein the phosphodiesterase inhibitor is aminophylline.

* * * * *